United States Patent [19]

Suzuki et al.

[11] Patent Number: 5,270,303

[45] Date of Patent: Dec. 14, 1993

[54] CHONDROMODULIN-II PROTEIN

[75] Inventors: Fujio Suzuki, Toyonaka; Yuji Hiraki, Takatsuki; Jun Kondo, Machida; Akihito Kamizono, Machida; Hideho Tanaka, Machida; Yutaka Teranishi, Sagamihara, all of Japan

[73] Assignee: Mitsubishi Kasei Corporation, Tokyo, Japan

[21] Appl. No.: 924,753

[22] Filed: Aug. 4, 1992

[30] Foreign Application Priority Data

Aug. 5, 1991 [JP] Japan .................................. 3-195495

[51] Int. Cl.$^5$ ........................ A61K 37/02; C07K 7/04
[52] U.S. Cl. ..................................... 514/21; 530/350; 530/399
[58] Field of Search .................. 514/21; 530/350, 399

[56] References Cited

U.S. PATENT DOCUMENTS

| | | | |
|---|---|---|---|
| 4,746,729 | 5/1988 | Kuettner et al. | 530/353 |
| 4,761,471 | 8/1988 | Urist | 530/350 |
| 4,804,744 | 2/1989 | Sen | 530/350 |
| 4,877,864 | 10/1989 | Wang et al. | 530/324 |
| 5,106,626 | 4/1992 | Parsons et al. | 530/350 X |

OTHER PUBLICATIONS

The Journal of Biological Chemistry vol. 265 No. 17, Jun. 15, 1990 pp. 9628-9633, "An 18-kDa Glycoprotein from Bovine Nasal Cartilage" Neame et al.
Biochemical and Biophysical Research Communications vol. 175, No. 3, Mar. 29, 1991 "Molecular Cloning of a New Class of Cartilage-Specific Matrix, Chondromodulin-I, Which Stimulates Growth of Cultured Chondrocytes" Hiraki et al. pp. 971-977.
Cell vol. 59, 1115-1125, Dec. 22, 1989 "The v-myb Oncogene Product Binds to and Activates the Promyelocyte-Specific mim-1 Gene" Ness et al.

Primary Examiner—Michael G. Wityshyn
Assistant Examiner—C. Sayala
Attorney, Agent, or Firm—Wenderoth, Lind & Ponack

[57] ABSTRACT

A novel chondromodulin-II protein having a molecular weight of about 16,000 dalton on SDS-PAGE, capable of stimulating the growth of chondrocytes with or without fibroblast growth factor and promoting the differential potency of said cells, and a pharmaceutical composition containing said protein as an active ingredient.

5 Claims, 6 Drawing Sheets

CHONDROMODULIN-II PROTEIN

BACKGROUND OF THE INVENTION

1. Field of the Invention

This invention relates to a novel chondromodulin protein. More particularly, it relates to chondromodulin-II protein capable of stimulating the growth of chondrocytes in the presence or absence of fibroblast growth factor and promoting the differential potency of said cells, and a pharmaceutical composition containing said protein as an active ingredient.

2. Description of Related Art

Almost all the bones of mammals, except for the flat bones such as cranial bone and the like, are formed through a mechanism called "intracartilaginous ossification", which comprises expression of primordial chondrocytes during the embryonic stage, growth and differentiation of said cartilaginous cells, generation of primordial cartilages such as proteoglycan, collagen II, collagen IX collagen X and the like, infiltration of capillary vessels which is accompanied by the decomposition of ground substance of cartilage and progression of calcification around the vesicles of said ground substance, and the replacement thereof with bone as the final step. Thus, the cartilage metabolism plays a significantly important role in the bone-formation, especially in the elongation of a bone along the axis.

It has been known that a variety of hormones and growth factors participate in the bone-formation (osteogenesis) process, including insulin-like growth factor (IGF1, IGF2), fibroblast growth factor (FGF), growth hormone, tumor cell growth factor (TGF-β) and the like. It has also been suggested that a certain active factor exists in cartilage, which stimulates the growth and differentiation of chondrocytes. Neam et al. [Peter J. Neam et al., Journal of Biological Chemistry Vol.265, No.17, 9628-9633, (1990)] reported that they separated from No.17, 9628-9633 bovine cartilage a sugar protein having a molecular weight of 18,000 dalton during the study for the identification of constitutive proteins in cartilage. However, they still have not elucidated the biological functions of said sugar protein.

The expression of the growth and differentiation of chondrocytes plays an important role in the course of recovery from fracture or various cartilage diseases as follows: inflammatory reaction at the injured site, growth of the periost-derived cells, expression and growth of chondrocytes, synthesis of extra-cellular ground substances, calcification of said substances, and replacement thereof with bone tissues. As can be easily understood, the growth of cartilage tissue at the site of fracture is essential for the formation of bone tissue. Additionally, it is obvious that the growth of the chondrocytes is also important for the recovery from cartilage diseases accompanied by cartilage destruction or injury. However, there have not been provided any substance which can stimulate the growth of chondrocytes, such substance thereby being useful as an active ingredient for the treatment of the above-mentioned diseases or disorders.

SUMMARY OF THE INVENTION

Some of the present inventors have isolated and purified a novel sugar protein (referred to as "chondromodulin-I protein") which has a molecular weight of about 26,000 dalton and an ability to stimulate the growth of chondrocytes from cartilage of fetal bovine for the first time (see, Biochemical and Biophysical Research Communications, Vol. 175, No. 3, 971-977, 1991 and European Patent Publication No. 0473080).

The present inventors have intensively studied this problem with the aim of obtaining other factor(s) having a chondrocyte-stimulating activity and have now succeeded in the isolation of a novel protein capable of stimulating the growth of chondrocytes, which has a molecular weight of about 16,000 dalton.

Thus, the present invention provides a novel chondromodulin-II protein characterized in that it has the following physicochemical properties:

a) a molecular weight of about 16,000 dalton on SDS-polyacrylamide gel electrophoresis;

b) an ability to stimulate the growth of chondrocytes in the presence or absence of fibroblast growth factor; and c) an ability to promote the differential potency of said chondrocytes.

The chondromodulin-II protein of the invention is expected to be useful in the treatment of fracture, various cartilage diseases and the like.

Purification of the novel chondromodulin-II protein can be conducted by any of the conventional procedures known to those skilled in the art. As will be hereinafter described in detail in the Examples, the chondromodulin-II protein was purified by crushing cartilage of fetal bovine, separating the supernatant by centrifugation, fractionating and concentrating the supernatant by ultrafiltration, further fractionating the concentrate by a molecular sieve chromatography on Sephacryl S200 column (Pharmacia) and the like, adsorbing onto a heparin-Toyopearl affinity column (Toso, Inc.) and eluting with, for example, a buffer containing 0.5M NaCl, purifying the resultant product repeatedly by chromatography on YMCpack C8 column (YMC, Inc.) while changing the elution conditions. Thus purified protein of the invention has a molecular weight of about 16,000 dalton on SDS-PAGE, and also has the activities of stimulating the growth of chondrocytes in the presence or absence of fibroblast growth factor (FGF) and promoting the differential potency of chondrocytes. The amino acid sequence of the purified peptide was then determined.

The chondromodulin-II protein of the invention comprises an amino acid sequence of SEQ ID NO: 1 at its N-terminal region and the partial amino acid sequences of SEQ ID NO: 2, 3 and 4. Further, the chondromodulin-II protein of the invention preferably comprises a partial amino acid sequences of SEQ ID NO: 5 to 14. The amino acid sequence of the full length chondromodulin-II protein is shown in SEQ ID NO: 15.

Once the amino acid sequence of chondromodulin-II protein is determined, it is easy to obtain active derivatives of chondromodulin-II protein, which falls within the scope of the invention, by conventional methods which leads to the deletion, replacement, modification or addition of amino acids without changing the properties of chondromodulin-II protein. Therefore, this invention also provides chondromodulin-II protein derivatives obtained by conventional methods.

DETAILED DESCRIPTION OF PREFERRED EMBODIMENTS

Biological activities of chondromodulin protein can be determined according to the Suzuki's methods as described in Example 6 (Suzuki, et al., Methods in Enzymology, 146; 313–320, 1987).

Thus, primary cells are isolated from growing costal cartilage obtained from a rabbit and grown in a 96-well plate. When the culture become confluent, [$^3$H] thymidine and 0.06 to 20 ng/ml of chondromodulin-II protein, and 0.04 ng/ml of FGF are added to the plate and the uptake of [$^3$H] thymidine is determined.

When the chondromodulin-II protein of the invention is used in clinical treatment, especially in the treatment of fracture or various cartilage disease, about 1 ng to 100 μg of said protein may be applied or injected locally to the site of fracture or cartilage disease by surgical treatment after mixing with, impregnating into, or applying onto a physiologically acceptable carrier, solvent, excipient or the like. Examples of physiologically acceptable carriers are bio-adhesives for surgery, including collagen, aterocollagen, gelatin, hyaluronic acid, polyethylene glycol, polylactose, bone cement, hydroxyapatite, ceramics, carbon fiber, fibrin, starch and the like. The chondromodulin-II protein also can be administered conventionally by injecting intravenously, subcutaneously for the treatment of various cartilage diseases.

Following Examples further illustrate in detail the invention disclosed, but should not be construed to limit the invention.

Example 1

Purification of Chondromodulin-II Protein

Fetal bovine cartilage (5 kg) was crushed into pieces (several mm in size) and homogenized in 10 times volume per weight of A buffer (1M guanidine hydrochloride, 0.1M 6-amino-n-caproic acid, 0.02M 2-(N-morpholino) ethanesulfonic acid, pH 6.0) by means of Politron.

The homogenate was stirred at 4° C. for 48 hr and centrifuged at 10,000×g for 20 min to separate the supernatant. The supernatant was added with cold acetone gradually to the final concentration of 45% and centrifuged at 4,000 rpm for 30 min to pellet the precipitates. To the supernatant was added cold acetone gradually to the final concentration of 65% and the mixture centrifuged at 4,000 rpm for 30 min to recover precipitates in fractions of acetone concentration of 45 to 65%. The pellet was dissolved in 6 L of B buffer (4M guanidine hydrochloride, 0.1M 6-amino-n-caproic acid, 1M NaCl, 0.02M Tris-HCl, pH 8.0) at 4° C. and centrifuged at 10,000 rpm for 30 min to remove insoluble materials as a pellet. The supernatant was concentrated to the final volume of 500 ml by a successive ultrafiltration using Amicon ultrafilter XM300, Amicon ultrafilter XM50, and Amicon ultrafilter YM10.

A portion of the concentrate (30 ml) was then subjected to molecular sieve chromatography using Sephacryl S200 column (2.6 cm diameter and 100 cm long) eluting with B buffer. Fractions eluted from 230 ml to 310 ml were pooled and dialyzed against distilled water at 4° C. for 2 days.

Figure 1:
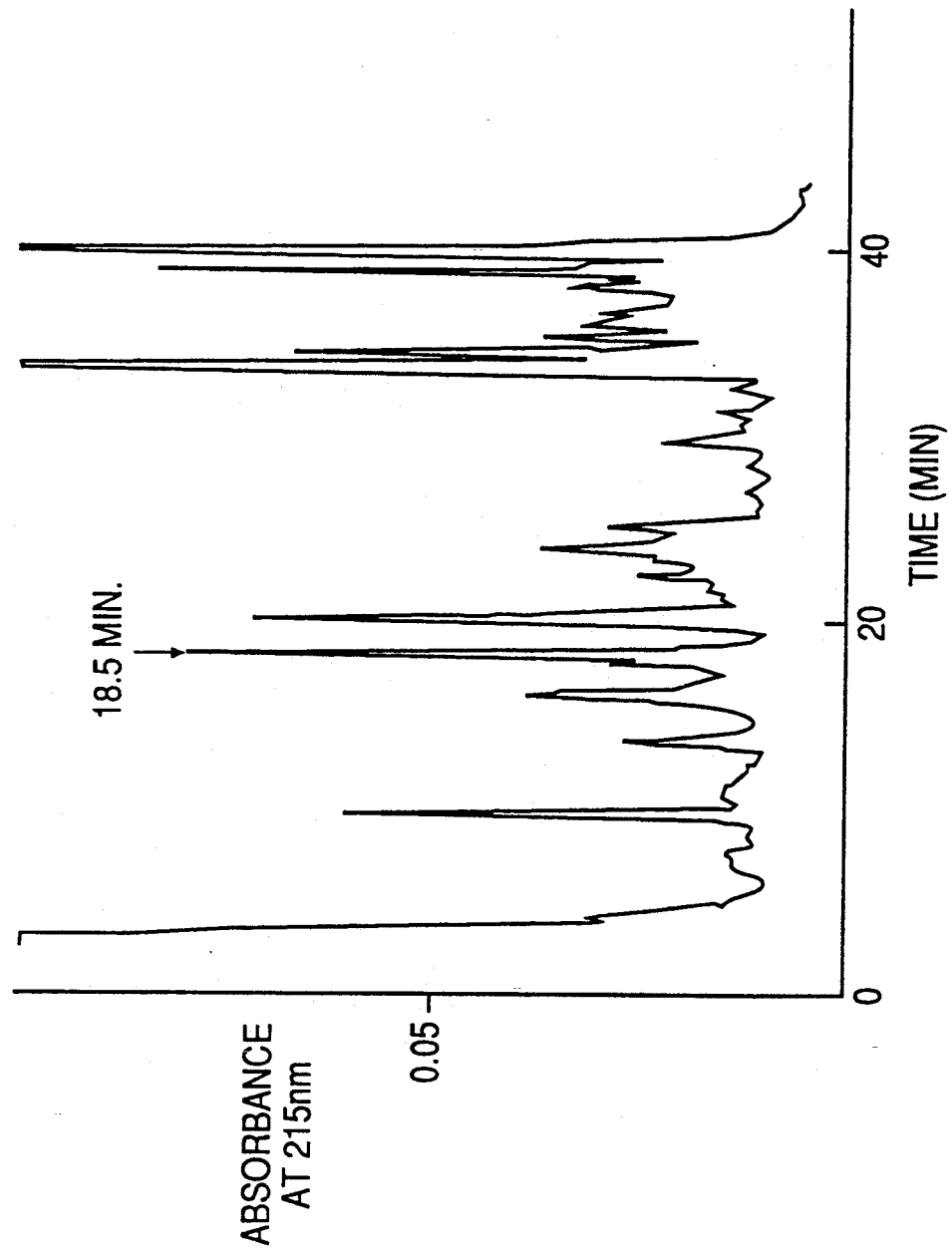
FIG. 1: An elution pattern of chondromodulin-II protein from YMCpack C8 column as described in Example 1.

The dialyzate was chromatographed on Heparin-Toyopearl column equilibrated with C buffer (0.15M NaCl, 0.03% CHAPS (surfactant), 0.025M sodium phosphate, pH 7.4). Thus, after washing the column thoroughly with C buffer, it was eluted with C buffer containing 0.5M NaCl. The fraction eluted with C buffer containing 0.5M NaCl was chromatographed on YMCpack C8 column (AP-802 S-5 300A C8, 0.46×15 cm) equilibrated with 30% acetonitrile/isopropyl alcohol (6.5/3.5, v/v) containing 0.1% TFA (trifluoroacetic acid). Elution was effected by successive linear gradients using the same solvent containing 30% to 45% of organic solvent for 30 min and then the same solvent containing 45% to 80% of organic solvent for 10 min. Active peaks were pooled and each peak was analyzed by the measurement of ultraviolet absorption at 215 nm. The elution pattern is given in FIG. 1. Among active fractions, one eluted at 18.5 min was dried under vacuum and the resultant sample was used for the determination of amino acid sequence.

Throughout the procedures described above, chondromodulin-II protein was fractionated and purified on the basis of the uptake of thymidine into cartilage cells as will be hereinafter described in Example 6.

Example 2

Amino Acid Analysis of Chondromodulin-II Protein

Chondromodulin-II protein purified in Example 1 was reduced by 2-mercaptoethanol in 6M guanidine hydrochloride, 0.002M ethylenediaminetetraacetic acid and 1M Tris-HCl (pH 8.5) at 40° C. for 2 hr. The reduced chondromodulin-II protein was then carboxymethylated by reacting with an equivalent concentration of monoiodoacetic acid at room temperature for 1 hr with shading in an atmosphere of nitrogen. The resultant mixture was dialyzed thoroughly against 1% acetic acid in a dark place, dried under vacuum, dissolved in 60 μl of 50% TFA, applied to a glass filter treated with polybrene and subjected to the Edman degradation for the determination of N-terminal amino acid sequence using 470A Sequencer (Applied Biosystems, Inc.). Phenylthiohydantoin (PTH) amino acid was identified using "MCIgelODS1Hu column" (0.46×15 cm) employing a single solvent elution with acetate buffer (10 mM acetate buffer, pH 4.7, 0.01% SDS, 38% acetonitrile) (flow rate: 1.2 ml/min; temperature: 43° C.; detection of PTH amino acid: absorbance at 269 nm).

Figure 2:
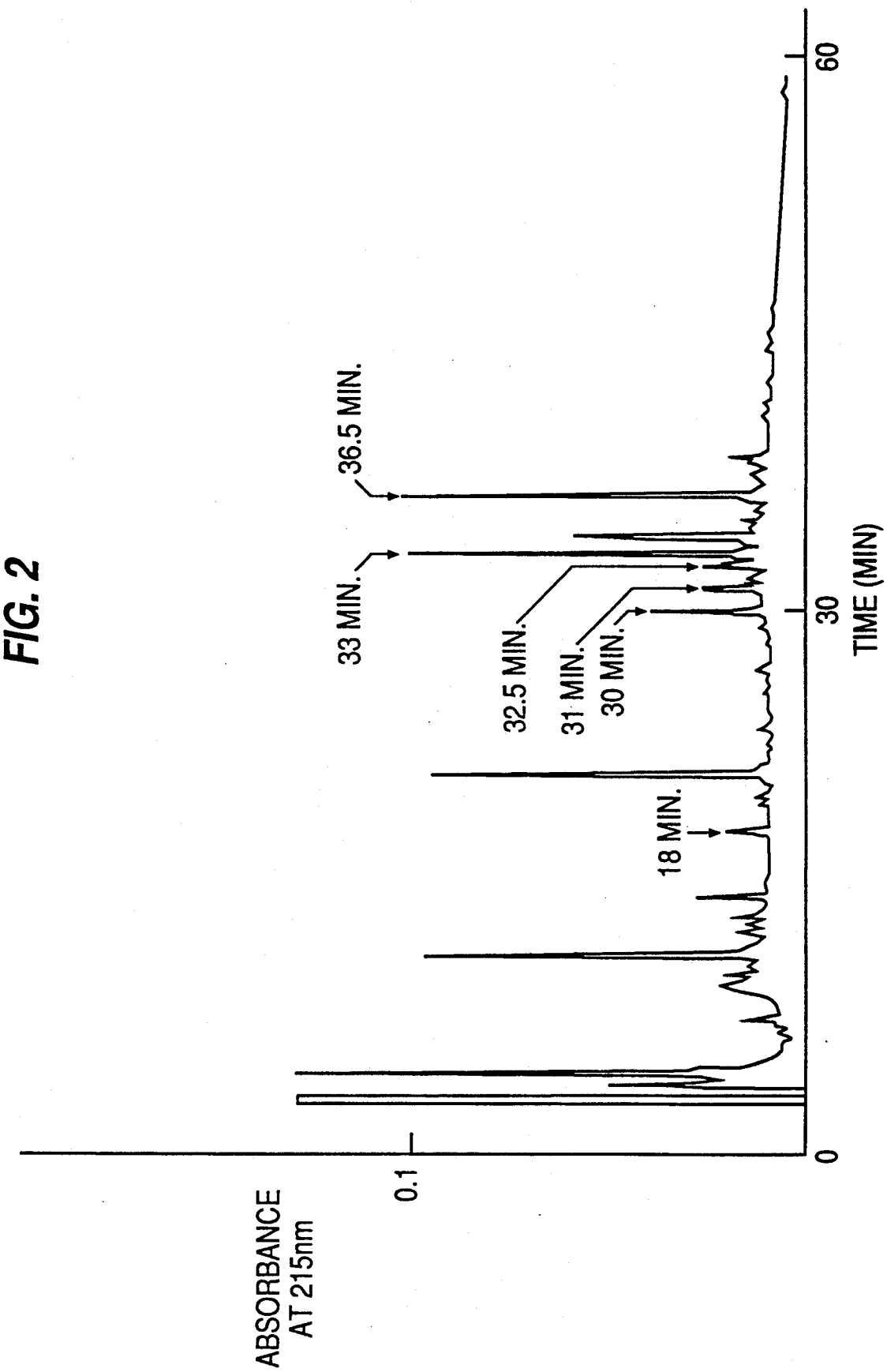
FIG. 2: An elution pattern of chondromodulin-II protein from Bakerbond C8 column as described in Example 2.

The carboxymethylated chondromodulin-II protein was then dissolved in 60 μl of 50 mM Tris-HCl buffer, pH 9.0, containing 5M urea and treated with lysylendopeptidase (Wako Junyaku, Japan) (enzyme:substrate=1:200) at 37° C. for 6 hr. The resultant mixture was chromatographed on Bakerbond C8 column (Bakerbond TM WP Octyl, 0.46×25 cm) equilibrated with 0.1% TFA eluting by a 60 min linear gradient of the solvent containing 0% to 60% of acetonitrile. Peaks were pooled and each peak was analyzed by the measurement of the ultraviolet absorption at 215 nm. The elution pattern is given in FIG. 2. Among fractions, those eluted at 31, 33, and 36.5 min were dried under vacuum and the resultant samples were further subjected to the Edman degradation using the same Sequencer in a similar manner as the above. As a result, the N-terminal amino acid sequence of chondromodulin-II protein was obtained (SEQ ID NO: 1). Also obtained are internal partial amino acid sequences of said protein corresponding to peptides eluted at 31, 33 and 36.5 min (SEQ ID NO: 2, 3 and 4, respectively). The purified chondromodulin-II protein, when applied to 12.5% SDS-polyacrylamide gel electrophoresis, gave a band corresponding to a molecular weight of about 16,000 dalton.

Example 3

Among fractions pooled in the above Example 2, those eluted at 18, 30, and 32.5 were further subjected to the Edman degradation using the same Sequencer in a similar manner as the above to yield internal partial amino acid sequences of SEQ ID NO: 5, 6 and 7, respectively.

Example 4

Figure 3:
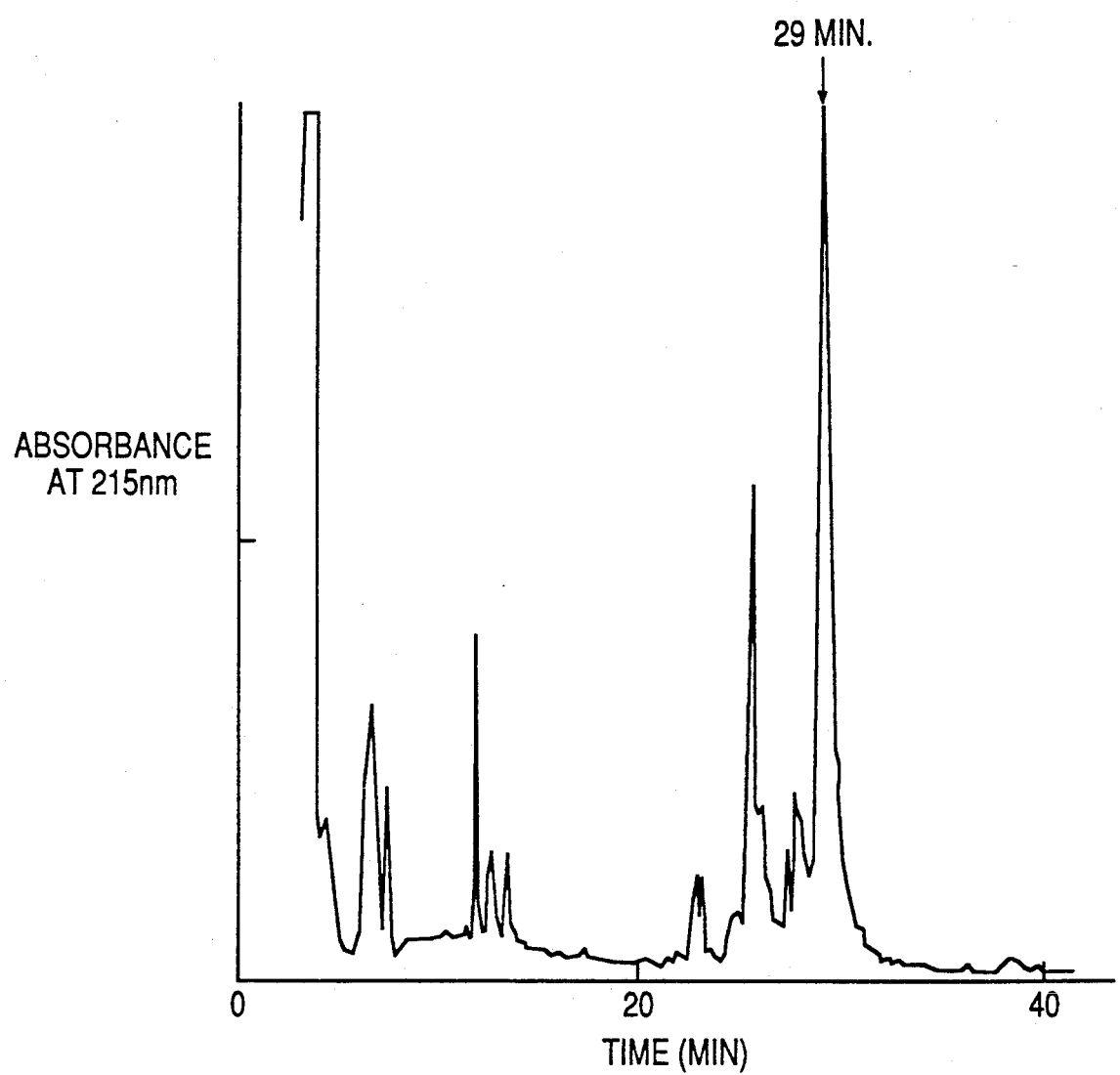
FIG. 3: An elution pattern of chondromodulin-II protein from Bakerbond C8 column as described in Example 4.
Figure 4:
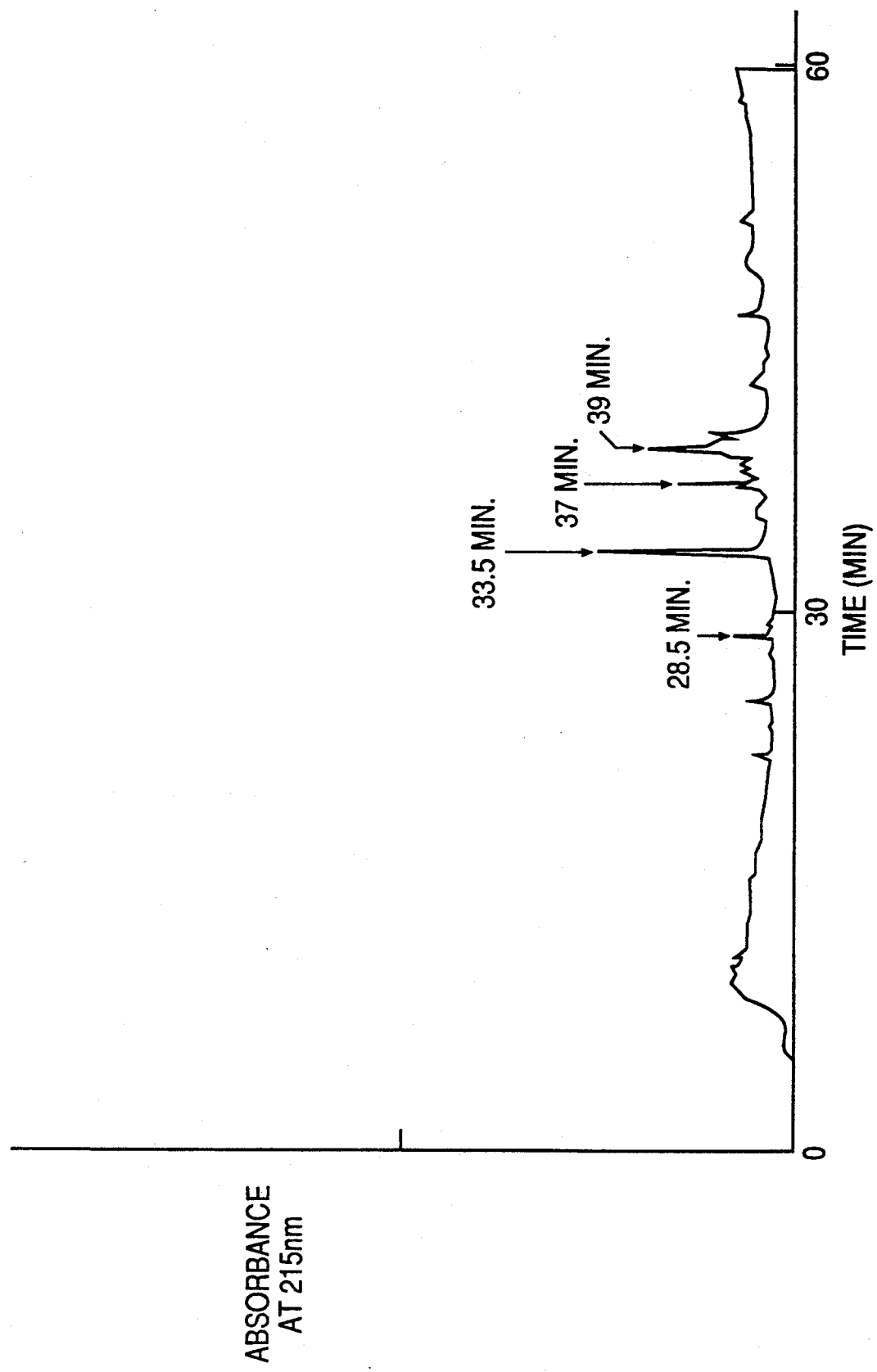
FIG. 4: An elution pattern of chondromodulin-II protein obtained by subjecting a fraction eluted at 29 min from Bakerbond C8 column as described in Example 4 to another Bakerbond C8 column treated with Staphylococcus V8 protease.

The carboxymethylated chondromodulin-II protein was dissolved in 70% formic acid and cleaved with 100 times molar excess of cyanogen bromide at 30° C. for 15 hr. The resultant mixture was chromatographed on Bakerbond C8 column (Bakerbond TM WP Octyl, 0.46×25 cm) equilibrated with 0.1% TFA eluting by a 40 min linear gradient of the solvent containing 0% to 60% of acetonitrile. Peaks were pooled and each peak was analyzed by measuring the absorbance at 215 nm. The elution pattern is given in FIG. 3. Fraction eluted at 29 min was dried under vacuum, dissolved in 0.1% ammonium hydrogencarbonate containing 2M urea, and treated with a Staphylococcus V8 protease (enzyme:substrate=1:50) at 37° C. for 15 hr, which was followed by a chromatography on Bakerbond C8 column under the same conditions as the above, employing the elution period of 60 min. Peaks were pooled and analyzed. The elution pattern is given in FIG. 4.

Among fractions, those eluted at 28.5, 33.5, 37, and 39 min were dried under vacuum and the resultant samples were further subjected to the Edman degradation using the same Sequencer to obtain internal partial amino acid sequences of SEQ ID NO: 8, 9, 10 and 11, respectively.

Example 5

Figure 5:
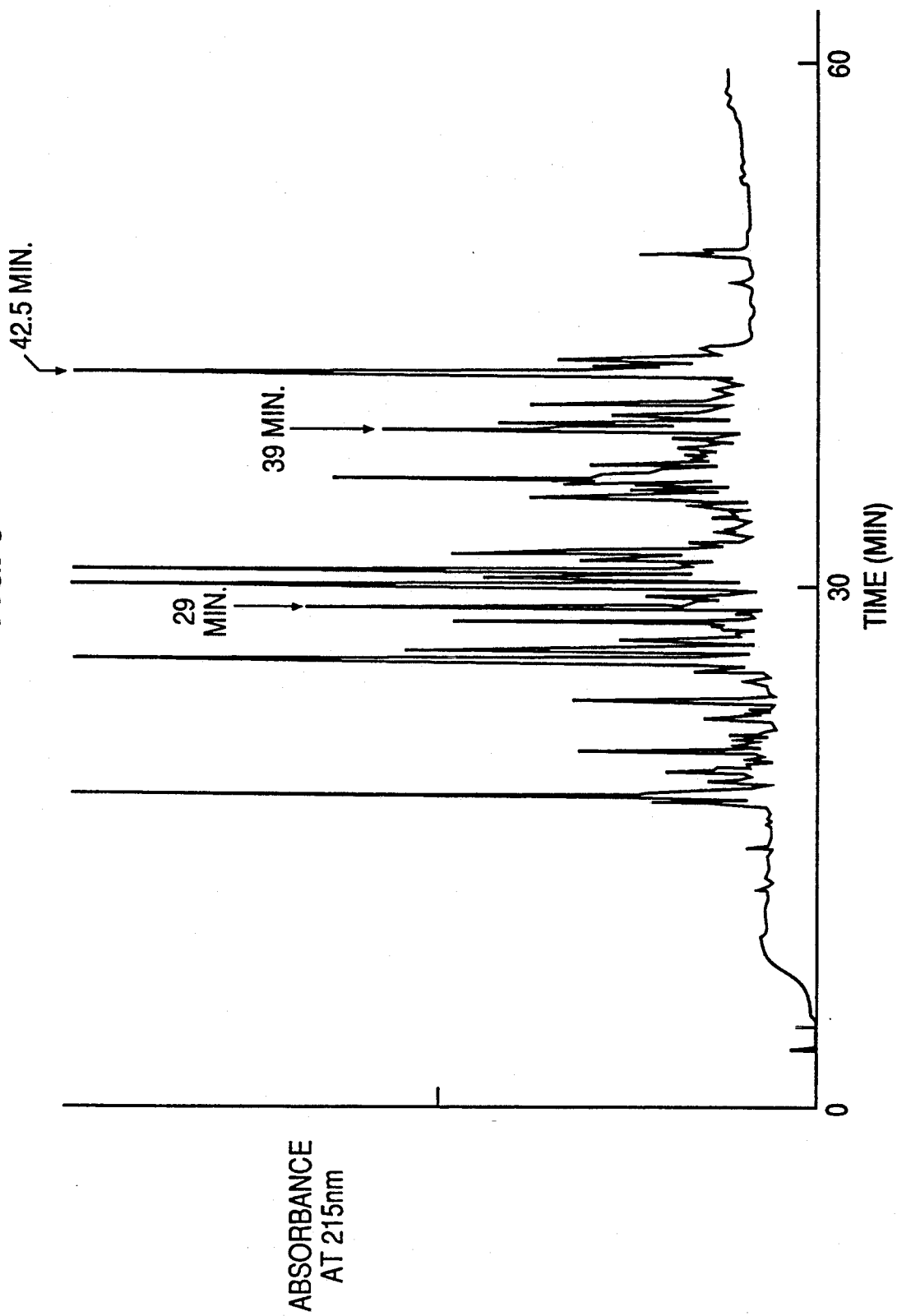
FIG. 5: An elution pattern of chondromodulin-II protein from Bakerbond C8 column as described in Example 5.

The carboxymethylated chondromodulin-II protein was dissolved in 1M ethylmorpholine/acetate buffer. To the solution was added 3 μl of acetic anhydride at 15-min interval (two times) at room temperature and dried under vacuum. After addition of 100 μl of water, it was dried under vacuum and dissolved in 0.1% ammonium hydrogencarbonate containing 2M urea. The resultant solution was treated with TPCK-trypsin (enzyme:substrate=1:50) at 37° C. for 15 hr, and then with chymotrypsin (enzyme:substrate=1.50) at 37° C. for 15 hr, which was followed by the treatment by a chromatography in the same manner as that described in Example 2. Peaks were pooled and analyzed. The elution pattern is given in FIG. 5.

Among fractions, those eluted at 29, 39, and 42.5 min were dried under vacuum and the resultant samples were further subjected to the Edman degradation using the same Sequencer to obtain internal partial amino acid sequences of SEQ ID NO: 12, 13, and 14, respectively.

The amino acid sequence of chondromodulin-II protein of full length was obtained by aligning N-terminal amino acid sequence (SEQ ID NO: 1) and internal partial amino acid sequences (SEQ ID NO: 2 to 14) and shown in SEQ ID NO: 15.

Example 6

Evaluation of Activities of Chondromodulin-II Protein

The isolation and cultivation of cells and the evaluation of activities of chondromodulin-II protein purified above were carried out substantially in accordance with a known method (Suzuki, et al, Methods in Enzymology, 146: 313-320, 1987). Cells were isolated from growing costal cartilage excised from a young New Zealand strain rabbit (400-600 g in weight) and suspended into a 1:1 mixture (hereinafter, referred to as FAD medium) of Ham's F-12 medium and Durbecco's modified medium containing 10% fetal bovine serum (FCS) at a cell density of $10^5$ cells/ml. The cell suspension (0.1 ml) was dispersed into 96-well plate, which had been treated by coating with type I collagen solution (50 μg/ml) overnight and washing with FAD medium, and incubated at 37° C. under an atmosphere of 5% $CO_2$ while changing the medium every other day.

Figure 6:
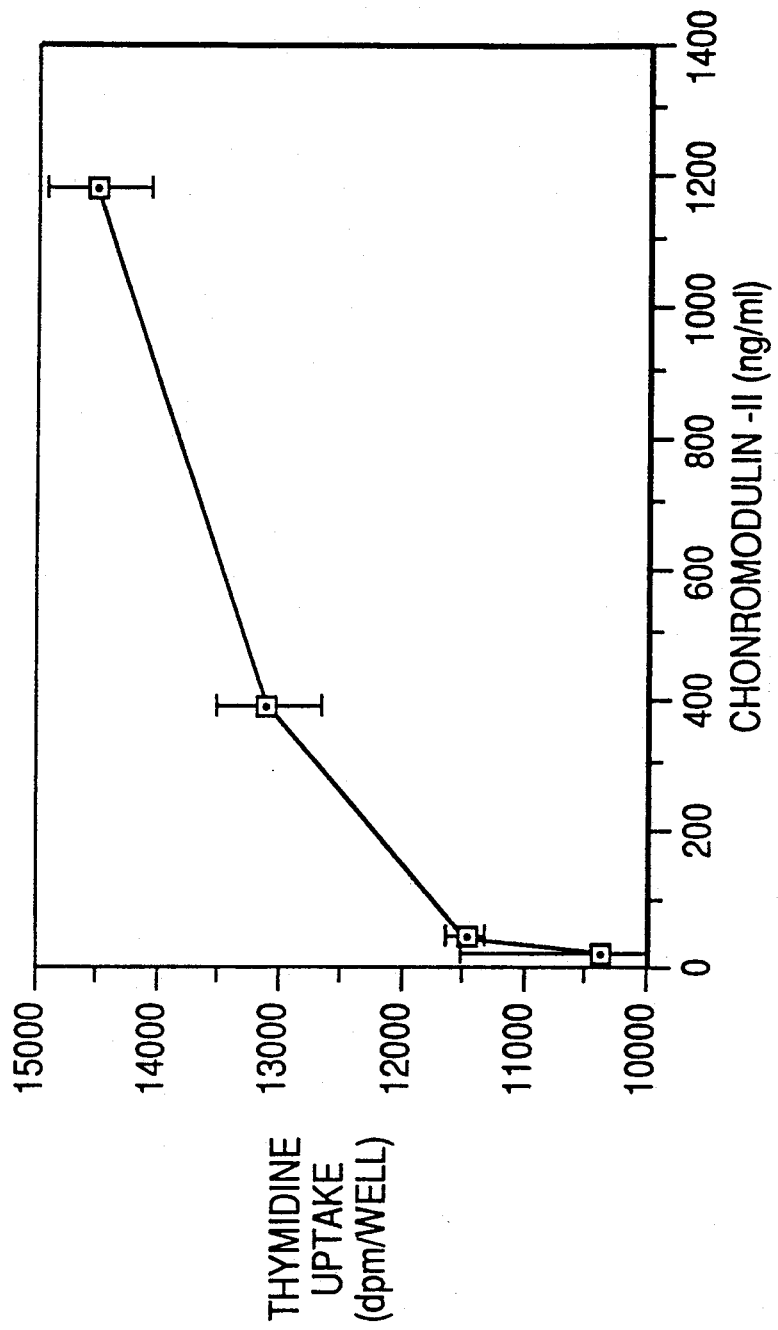
FIG. 6: DNA-synthetic activity of chondromodulin-II protein evaluated on the basis of the uptake of thymidine.

The DNA-synthetic activity was evaluated as follows. After cells were grown in the above 96-well plate until the culture became confluent, they were transferred into FAD medium containing 0.3% FCS and grown for 24 hr. The culture was incubated for 22 hr in 0.1 ml of FAD medium containing 0.06 to 20 ng of chondromodulin-II protein, 0.04 ng of FGF (fibroblast growth factor) and 0.3% FCS. The cultivation was continued another 4 hr after the addition of 10 μl of [$^3$H] thymidine (130 μCi/ml) and cells were washed three times with ice-cold phosphate-buffered saline (20 mM phosphate buffer, pH7.0, 0.15M sodium chloride), extracted with 5% trichloroacetic acid and then with ethanol/ether (3:1, v/v). After the extraction, the precipitate left was dissolved in 0.3M sodium hydroxide, neutralized with 1/20 volume of 6N HCl and the radioactivity was detected by means of a scintillation counter. Results are given in FIG. 6. FIG. 6 shows that the uptake of radioactive thymidine in the presence of 1200 ng/ml of chondromodulin-II protein was apparently increased and it as about 3.5 folds of that observed in the absence of FGF (4066±864 dpm/well) and about 1.4 folds of that observed in the presence of 0.4 ng of FGF (10626±1327 dpm/well), demonstrating that the chondromodulin-II protein possesses a potent stimulating effect on the growth of chondrocytes.

---

What is claimed is:

1. A substantially purified and isolated chondromodulin-II protein which has the following properties:
   a) a molecular weight of about 16,000 dalton on SDS-polyacrylamide gel electrophoresis;
   b) an ability to stimulate the growth of chondrocytes in the presence or absence of fibroblast growth factor;
   c) an ability to promote the differential potency of said chondrocytes; and
   d) an amino acid sequence comprising the N-terminal amino acid sequence of SEQ ID NO: 1 and the partial amino acid sequences of SEQ ID NOS: 2, 3 and 4.

2. The chondromodulin-II protein of claim 1 which comprises the N-terminal amino acid sequence of SEQ ID NO: 1 and partial amino acid sequences of SEQ ID NO: 2 to 14.

3. The chondromodulin-II protein of claim 1 which comprises the amino acid sequence of SEQ ID NO: 15.

4. A pharmaceutical composition containing, as an active ingredient, an effective amount of a chondromodulin-II protein of claim 1 together with a pharmaceutically acceptable carrier, excipient or solvent therefor.

5. A pharmaceutical composition for stimulating the growth of chondrocytes which contains, as an active ingredient, an effective amount of a chondromodulin-II protein of claim 1 together with a pharmaceutically acceptable carrier, excipient or solvent therefor.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL:

( i v ) ANTI-SENSE:

( v ) FRAGMENT TYPE: N-terminal fragment ( v i ) ORIGINAL SOURCE:
        ( A ) ORGANISM: bovine
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE: fetal cartilage
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:1:

```
Gly  Pro  Trp  Ala  Ile  Ile  Cys  Ala  Gly  Lys
 1                  5                        10

Ser  Ser  Asn  Glu  Ile  Arg  Thr  Cys  Asp  Gly
                    15                       20

His  Gly  Cys  Gly  Gln  Tyr  Thr  Ala  Gln  Arg
                    25                       30

Asn  Gln  Lys  Leu  His  Gln  Gly  Val  Asp  Val
                    35                       40

Leu
```

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear

```
          ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
                  ( A ) ORGANISM: bovine
                  ( B ) STRAIN:
                  ( C ) INDIVIDUAL ISOLATE:
                  ( D ) DEVELOPMENTAL STAGE:
                  ( E ) HAPLOTYPE:
                  ( F ) TISSUE TYPE: fetal cartilage
                  ( G ) CELL TYPE:
                  ( H ) CELL LINE:
                  ( I ) ORGANELLE:

( v i i ) IMMEDIATE SOURCE:
                  ( A ) LIBRARY:
                  ( B ) CLONE:

( v i i i ) POSITION IN GENOME:
                  ( A ) CHROMOSOME/SEGMENT:
                  ( B ) MAP POSITION:
                  ( C ) UNITS:

( i x ) FEATURE:
                  ( A ) NAME/KEY:
                  ( B ) LOCATION:
                  ( C ) IDENTIFICATION METHOD:
                  ( D ) OTHER INFORMATION:

( x ) PUBLICATION INFORMATION:
                  ( A ) AUTHORS:
                  ( B ) TITLE:
                  ( C ) JOURNAL:
                  ( D ) VOLUME:
                  ( E ) ISSUE:
                  ( F ) PAGES:
                  ( G ) DATE:
                  ( H ) DOCUMENT NUMBER:
                  ( I ) FILING DATE:
                  ( J ) PUBLICATION DATE:
                  ( K ) RELEVANT RESIDUES IN SEQ ID NO:

( x i ) SEQUENCE DESCRIPTION: SEQ ID NO:2:

Asn  Ala  Ile  Asn  Asn  Gly  Val  Arg  Ile
 1                  5

( 2 ) INFORMATION FOR SEQ ID NO:3:

( i ) SEQUENCE CHARACTERISTICS:
                  ( A ) LENGTH: 19 amino acids
                  ( B ) TYPE: amino acid
                  ( C ) STRANDEDNESS: single
                  ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
                  ( A ) ORGANISM: bovine
                  ( B ) STRAIN:
                  ( C ) INDIVIDUAL ISOLATE:
                  ( D ) DEVELOPMENTAL STAGE:
                  ( E ) HAPLOTYPE:
                  ( F ) TISSUE TYPE: fetal cartilage
                  ( G ) CELL TYPE:
                  ( H ) CELL LINE:
                  ( I ) ORGANELLE:

( v i i ) IMMEDIATE SOURCE:
                  ( A ) LIBRARY:
```

(B) CLONE:

(viii) POSITION IN GENOME:
          (A) CHROMOSOME/SEGMENT:
          (B) MAP POSITION:
          (C) UNITS:

(ix) FEATURE:
          (A) NAME/KEY:
          (B) LOCATION:
          (C) IDENTIFICATION METHOD:
          (D) OTHER INFORMATION:

(x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO:3:

Leu His Gln Gly Val Asp Val Leu Cys Ser
 1               5                   10

Asp Gly Ser Thr Val Tyr Ala Pro Phe
                15

(2) INFORMATION FOR SEQ ID NO:4:

(i) SEQUENCE CHARACTERISTICS:
          (A) LENGTH: 18 amino acids
          (B) TYPE: amino acid
          (C) STRANDEDNESS: single
          (D) TOPOLOGY: linear (ii) MOLECULE TYPE: protein (iii) HYPOTHETICAL:

(iv) ANTI-SENSE:

(v) FRAGMENT TYPE: internal fragment (vi) ORIGINAL SOURCE:
          (A) ORGANISM: bovine
          (B) STRAIN:
          (C) INDIVIDUAL ISOLATE:
          (D) DEVELOPMENTAL STAGE:
          (E) HAPLOTYPE:
          (F) TISSUE TYPE: fetal cartilage
          (G) CELL TYPE:
          (H) CELL LINE:
          (I) ORGANELLE:

(vii) IMMEDIATE SOURCE:
          (A) LIBRARY:
          (B) CLONE:

(viii) POSITION IN GENOME:
          (A) CHROMOSOME/SEGMENT:
          (B) MAP POSITION:
          (C) UNITS:

(ix) FEATURE:
          (A) NAME/KEY:
          (B) LOCATION:
          (C) IDENTIFICATION METHOD:
          (D) OTHER INFORMATION:

(x) PUBLICATION INFORMATION:
          (A) AUTHORS:
          (B) TITLE:
          (C) JOURNAL:
          (D) VOLUME:

( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:4:

Val Tyr Pro Gly Ile Gln Ser His Ile His
 1               5                   1 0

Ile Glu Asn Cys Asp Leu Ser Asp
                1 5

( 2 ) INFORMATION FOR SEQ ID NO:5:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
                ( A ) ORGANISM: bovine
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE: fetal cartilage
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:5:

Ile Met Gly Gln Glu Lys
 1               5

( 2 ) INFORMATION FOR SEQ ID NO:6:

( i ) SEQUENCE CHARACTERISTICS:
                ( A ) LENGTH: 5 amino acids (B) TYPE: amino acid
            (C) STRANDEDNESS: single
            (D) TOPOLOGY: linear (ii) MOLECULE TYPE: protein (iii) HYPOTHETICAL:

(iv) ANTI-SENSE:

(v) FRAGMENT TYPE: internal fragment (vi) ORIGINAL SOURCE:
            (A) ORGANISM: bovine
            (B) STRAIN:
            (C) INDIVIDUAL ISOLATE:
            (D) DEVELOPMENTAL STAGE:
            (E) HAPLOTYPE:
            (F) TISSUE TYPE: fetal cartilage
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:6:

Met Phe Tyr Ile Lys
1               5

(2) INFORMATION FOR SEQ ID NO:7:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (iii) HYPOTHETICAL:

(iv) ANTI-SENSE:

(v) FRAGMENT TYPE: internal fragment (vi) ORIGINAL SOURCE:
            (A) ORGANISM: bovine
            (B) STRAIN:
            (C) INDIVIDUAL ISOLATE:
            (D) DEVELOPMENTAL STAGE:
            (E) HAPLOTYPE:
            (F) TISSUE TYPE: fetal cartilage
            (G) CELL TYPE:
            (H) CELL LINE:

( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:7:

Leu Gly Thr Leu Leu Pro Leu Gln Lys
 1                   5

( 2 ) INFORMATION FOR SEQ ID NO:8:

( i ) SEQUENCE CHARACTERISTICS:
                    ( A ) LENGTH: 11 amino acids
                    ( B ) TYPE: amino acid
                    ( C ) STRANDEDNESS: single
                    ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
                    ( A ) ORGANISM: bovine
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE: fetal cartilage
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:

```
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:8:
```

Asn Cys Asp Leu Ser Asp Pro Thr Val Tyr
 1               5                   1 0

Leu ( 2 ) INFORMATION FOR SEQ ID NO:9:

```
        ( i ) SEQUENCE CHARACTERISTICS:
                ( A ) LENGTH: 14 amino acids
                ( B ) TYPE: amino acid
                ( C ) STRANDEDNESS: single
                ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
                ( A ) ORGANISM: bovine
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE: fetal cartilage
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:9:
```

Phe Tyr Ile Lys Pro Ile Lys Tyr Lys Gly
 1               5                   1 0

Ser Ile Lys Lys ( 2 ) INFORMATION FOR SEQ ID NO:10:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
    ( A ) ORGANISM: bovine
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE: fetal cartilage
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:10:

Lys Leu Gly Thr Leu Leu Pro Leu Gln Lys
1           5                   10

Val Tyr Pro Gly ( 2 ) INFORMATION FOR SEQ ID NO:11:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
    ( A ) ORGANISM: bovine
    ( B ) STRAIN:
    ( C ) INDIVIDUAL ISOLATE:
    ( D ) DEVELOPMENTAL STAGE:

(E) HAPLOTYPE:
(F) TISSUE TYPE: fetal cartilage
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:11:

Lys Pro Tyr Lys Asn Lys Asn Ala Ile Asn
 1               5                  10

Asn Gly Val Arg Ile Ser Gly Gly
              15

(2) INFORMATION FOR SEQ ID NO:12:

(i) SEQUENCE CHARACTERISTICS:
(A) LENGTH: 19 amino acids
(B) TYPE: amino acid
(C) STRANDEDNESS: single
(D) TOPOLOGY: linear (ii) MOLECULE TYPE: protein (iii) HYPOTHETICAL:

(iv) ANTI-SENSE:

(v) FRAGMENT TYPE: internal fragment (vi) ORIGINAL SOURCE:
(A) ORGANISM: bovine
(B) STRAIN:
(C) INDIVIDUAL ISOLATE:
(D) DEVELOPMENTAL STAGE:
(E) HAPLOTYPE:
(F) TISSUE TYPE: fetal cartilage
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:

( C ) IDENTIFICATION METHOD:
( D ) OTHER INFORMATION:

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:12:

Ala Pro Phe Thr Gly Lys Ile Met Gly Gln
1               5                   10

Glu Lys Pro Tyr Lys Asn Lys Asn Ala
                15

( 2 ) INFORMATION FOR SEQ ID NO:13:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
( A ) ORGANISM: bovine
( B ) STRAIN:
( C ) INDIVIDUAL ISOLATE:
( D ) DEVELOPMENTAL STAGE:
( E ) HAPLOTYPE:
( F ) TISSUE TYPE: fetal cartilage
( G ) CELL TYPE:
( H ) CELL LINE:
( I ) ORGANELLE:

( v i i ) IMMEDIATE SOURCE:
( A ) LIBRARY:
( B ) CLONE:

( v i i i ) POSITION IN GENOME:
( A ) CHROMOSOME/SEGMENT:
( B ) MAP POSITION:
( C ) UNITS:

( i x ) FEATURE:
( A ) NAME/KEY:
( B ) LOCATION:
( C ) IDENTIFICATION METHOD:
( D ) OTHER INFORMATION:

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:13:

```
Ile  Ser  Gly  Gly  Gly  Phe  Cys  Ile  Lys  Met
 1              5                        10
Phe
```

( 2 ) INFORMATION FOR SEQ ID NO:14:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
        ( A ) ORGANISM: bovine
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE: fetal cartilage
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:14:

```
Lys  Gly  Ser  Ile  Lys  Lys  Gly  Glu  Lys  Leu
 1              5                        10

Gly  Thr  Leu  Leu  Pro  Leu  Gln  Lys  Val  Tyr
                     15                        20

Pro  Gly  Ile  Gln  Ser  His  Ile
                    25
```

( 2 ) INFORMATION FOR SEQ ID NO:15:

( i ) SEQUENCE CHARACTERISTICS:
        ( A ) LENGTH: 133 amino acids
        ( B ) TYPE: amino acid
        ( C ) STRANDEDNESS: single
        ( D ) TOPOLOGY: linear ( i i ) MOLECULE TYPE: protein (iii) HYPOTHETICAL:

(iv) ANTI-SENSE:

(v) FRAGMENT TYPE:

(vi) ORIGINAL SOURCE:
(A) ORGANISM: bovine
(B) STRAIN:
(C) INDIVIDUAL ISOLATE:
(D) DEVELOPMENTAL STAGE:
(E) HAPLOTYPE:
(F) TISSUE TYPE: fetal cartilage
(G) CELL TYPE:
(H) CELL LINE:
(I) ORGANELLE:

(vii) IMMEDIATE SOURCE:
(A) LIBRARY:
(B) CLONE:

(viii) POSITION IN GENOME:
(A) CHROMOSOME/SEGMENT:
(B) MAP POSITION:
(C) UNITS:

(ix) FEATURE:
(A) NAME/KEY:
(B) LOCATION:
(C) IDENTIFICATION METHOD:
(D) OTHER INFORMATION:

(x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:15:

```
Gly Pro Trp Ala Ile Ile Cys Ala Gly Lys
 1               5                  10

Ser Ser Asn Glu Ile Arg Thr Cys Asp Gly
                15                  20

His Gly Cys Gly Gln Tyr Thr Ala Gln Arg
                25                  30

Asn Gln Lys Leu His Gln Gly Val Asp Val
                35                  40

Leu Cys Ser Asp Gly Ser Thr Val Tyr Ala
                45                  50

Pro Phe Thr Gly Lys Ile Met Gly Gln Glu
                55                  60

Lys Pro Tyr Lys Asn Lys Asn Ala Ile Asn
                65                  70

Asn Gly Val Arg Ile Ser Gly Gly Gly Phe
                75                  80

Cys Ile Lys Met Phe Tyr Ile Lys Pro Ile
                85                  90

Lys Tyr Lys Gly Ser Ile Lys Lys Gly Glu
                95                  100

Lys Leu Gly Thr Leu Leu Pro Leu Gln Lys
                105                 110

Val Tyr Pro Gly Ile Gln Ser His Ile His
```

```
            115                    120
Ile Glu Asn Cys Asp Leu Ser Asp Pro Thr
                 125                    130
Val Tyr Leu
```